United States Patent [19]

Anderson

[11] Patent Number: 5,258,051
[45] Date of Patent: Nov. 2, 1993

[54] SCENTED AIR FILTER

[76] Inventor: Phillip T. Anderson, 1717 E. Union Hills, #1114, Phoenix, Ariz. 85024

[21] Appl. No.: 947,458

[22] Filed: Sep. 21, 1992

[51] Int. Cl.$^5$ .............................................. A61L 9/04
[52] U.S. Cl. ................................... 55/279; 55/501; 55/511; 55/DIG. 31; 261/DIG. 65; 422/924
[58] Field of Search ............... 55/279, DIG. 31, 495, 55/501, 511; 261/DIG. 65; 422/124

[56] References Cited

U.S. PATENT DOCUMENTS

| | | | |
|---|---|---|---|
| 2,965,197 | 12/1960 | Dow et al. | 55/511 |
| 3,017,239 | 1/1962 | Rodman | 55/229 |
| 4,118,226 | 10/1978 | Bourassa | 55/279 |
| 4,604,114 | 8/1986 | Ward | 55/279 |
| 4,875,912 | 10/1989 | Fulmer | 55/279 |
| 4,959,087 | 9/1990 | Kappernaros | 55/279 |

Primary Examiner—Tim Miles
Attorney, Agent, or Firm—LaValle D. Ptak

[57] ABSTRACT

An air filter for use with a forced air handling system has a pad of air-permeable material held in a bordering frame. The bordering frame has a generally U-shaped cross section, with opposing legs extending a short distance over the edge of the pad of air-permeable material. The legs of the bordering frame have spaced apertures extending through them; and scented material is placed within the frame and located so that air passage through the apertures in the frame passes through the scented material to evaporate or volatilize the scented material and supply it to the filtered air flowing through the filter pad.

13 Claims, 1 Drawing Sheet

SCENTED AIR FILTER

BACKGROUND

Panel type, replaceable air filters are widely used in forced air heating and air conditioning systems. These filters often comprise a pad of air-permeable filtering material made of fiberglass or other suitable material. This pad is mounted in a frame, usually along with a reinforcing metal grid. The frame then is placed in the return air duct for the forced air system to remove dust particles and the like from the air flow. In time, the dust build-up on the filter becomes sufficient that the filter needs to be replaced or cleaned. The most popular filters are simply discarded and replaced with new filters. Consequently, they are inexpensively made, with the bordering frame for holding the metal support grid and the air-permeable filter pad being made of lightweight cardboard or the like.

There also is a large market for various products used to mask and control unwanted odors in homes and work places. Such products typically include air freshener sprays, blocks, electrically operated scent dispensers, candles, wicks, potpourri and the like. With all of these products, a number of drawbacks exist. With sprays, it is necessary to dispense the spray by hand in each room or area where the odor control is desired. With wicks, blocks, plug-in devices and the like, a number of them must be placed throughout the space in which the odor control is desired, in order to obtain the desired results. With all of these products, however, the benefits are relatively expensive and short-lived.

Attempts have been made to incorporate the release of odor control scents into the air handling system of furnaces and air conditioning systems. Three patents directed to a combination of scent release and air filtration are the patents to Ward U.S. Pat. No. 4,604,114; Fulmer U.S. Pat. No. 4,875,912; and Kappernaros U.S. Pat. No. 4,959,087.

The Ward patent is directed to a fragrance scented air filter, in which the otherwise standard disposable air filter includes two solid rods of scented material spanning the frame across the path of the air moving through the filter. The air which passes adjacent these rods absorbs the fragrance, which then is distributed by the air handling system in the building with which it is used.

The device of Fulmer places a scented evaporant packet in a cut-out portion of the filter, typically near a corner. A foil is placed over the evaporant packet; and when this foil is partially or fully removed, the evaporant is exposed to the air flowing in the return air duct. This packet, however, blocks the portion of the filter where it is placed.

The device shown in the patent to Kappernaros is an elongated bar of impregnated filter material, which is placed in a formed pocket on the edge of the frame around the air filter. A tear strip is provided over the material to expose various portions of the bar for scent release into the air stream passing through the filter.

The scented rods of Ward, and the packet of Fulmer are placed directly in the normal air path through the filter. Consequently, the area which is occupied by these devices effects a corresponding reduction in the air flow which passes through the filter. As a result, the area which is occupied by the scent releasing devices of Ward and Fulmer necessarily must be kept to as small a percentage of the overall area of the filter surface as possible. Since these devices also are placed in the main air flow path of air through the filter, they also are subjected to the maximum air flow through the filter; and therefore, the scent dispensing members must be fabricated to have a considerably lower volatility than would be necessary if they were not placed in the main air flow path.

The device of the Kappanaros patent does place the scented material out of the main air flow path of the filter. This device, however, requires a portion of the frame around the filter material to be enlarged to form the pocket in which the scent bar is placed. In addition, air flows past only one edge of the scent bar, the bulk of which is embedded in the frame of the air filter, in a position which prevents air from passing around it or through it.

In addition to providing scents for masking and controlling odors, interest also has been shown in dispensing anti-bacterial and/or anti-fungal agents into the duct work of a forced air heating or cooling system, for controlling bacteria, fungi and molds. Such materials also may be made in a form which sublimates or volatilizes as air passes over them, and can be formulated to function in the same manner as the release of scents described above in conjunction with the Ward, Fulmer and Kappanaros patents.

Accordingly, it desirable to provide an air filter system for use with a forced air heating or air conditioning system, which may be used to dispense scents or anti-bacterial and anti-fungal agents, without impairing the air flow through the filter, and without requiring dimensional modifications of the mechanical configurations of replaceable filters.

SUMMARY OF THE INVENTION

It is an object of this invention to provide an improved air filter.

It is another object of this invention to provide an improved disposable air filter incorporating a scent release medium in its construction.

It is an additional object of this invention to provide an improved disposable air filter panel with a scent release material incorporated into the frame thereof.

A further object of this invention is to provide an air filter comprised of air-permeable material mounted in a frame, which incorporates volatile scent material for release into the airstream of air moving through the air-permeable portion of the filter.

In accordance with a preferred embodiment of the invention, an air filter includes a pad of air-permeable filtering material. The pad of air-permeable filtering material is held in a bordering frame having a generally U-shaped cross section. Inwardly-turned legs of the U-shaped cross section extend a predetermined distance over the edge of the permeable material to hold it in place in the frame. The frame includes scented material, which sublimates or volatilizes in air; and the frame further includes a provision for directing air through the frame itself to volatilize the scented material in the frame.

DETAILED DESCRIPTION

Figure 1:
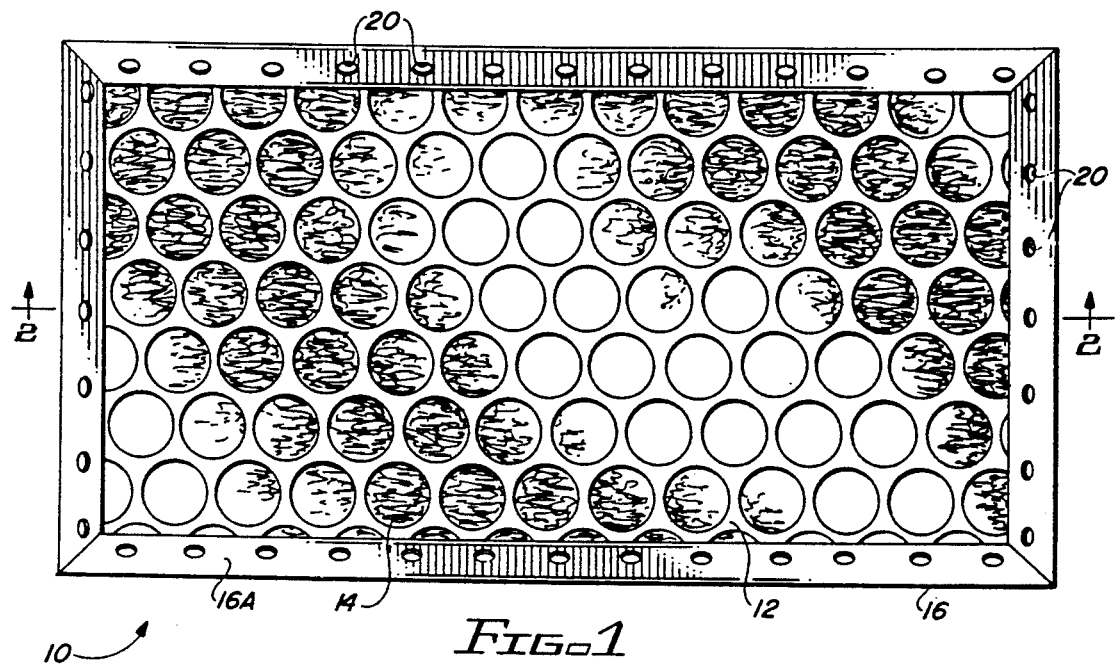
FIG. 1 is a top view of a preferred embodiment of the invention.

Reference now should be made to the drawing, in which the same reference numbers are used in the different figures to designate the same components. As illustrated, an air filter 10 is shown comprised of a thin pad of air-permeable fibrous material, such as fiberglass, covered by an open metallic grid 12, which serves to prevent the deformation of the relatively thin pad 14 and to retain the pad 14 in place against the flow of air through it in the direction shown in FIG. 2. The filter pad 14 and the grid 12 typically are held in a bordering frame 16 of cardboard, which, essentially, has a generally U-shaped cross section.

Figure 2:
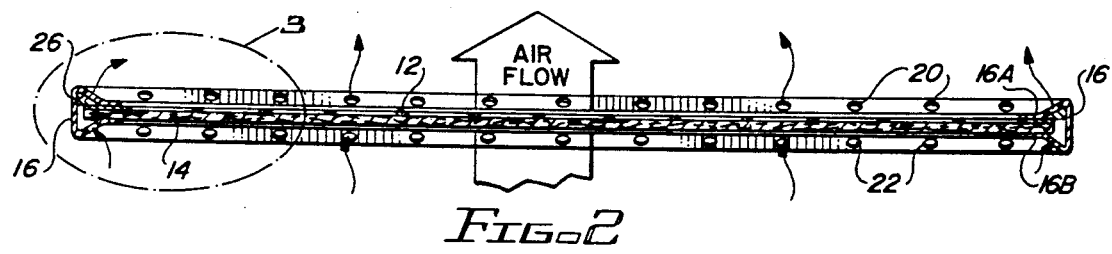
FIG. 2 is a cross-sectional view taken along the line 2—2 of FIG. 1.
Figure 3:
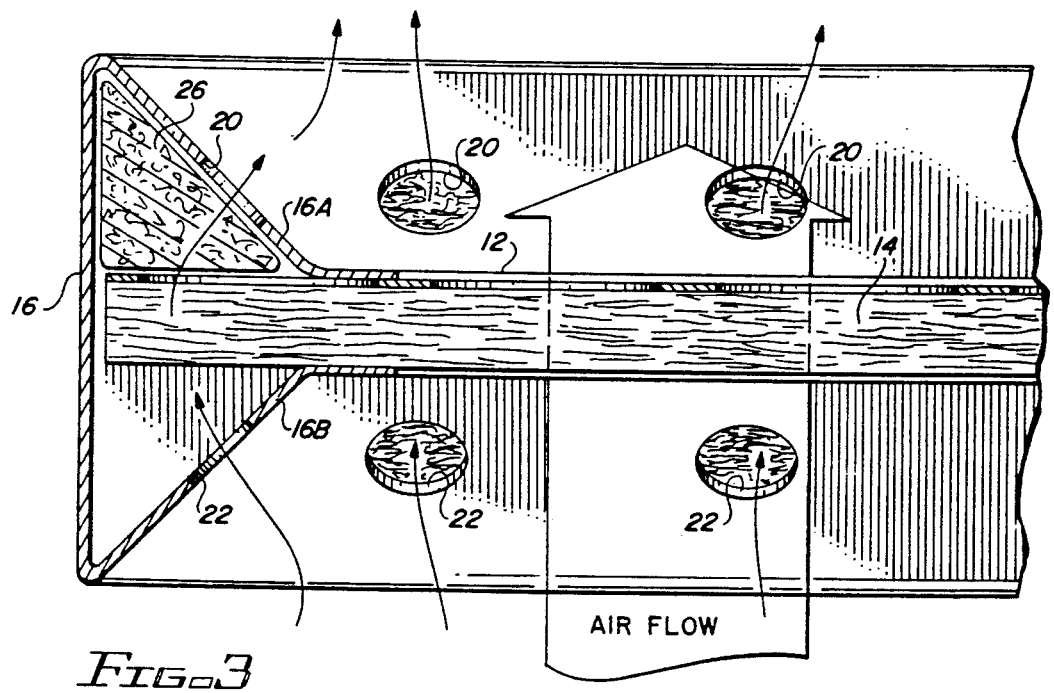
FIG. 3 is an enlarged cross section of the portion circled as 3 in FIG. 2.

The frame 16 is usually flat along the edges, in a plane perpendicular to the plane of the grid 12 and air-permeable filter material 14, as illustrated most clearly in FIGS. 2 and 3. The frame 16 then has a pair of inwardly-turned legs 16A and 16B (shown most clearly in FIG. 3), which are clamped down onto the metal retainer grid 12 and the pad 14, to sandwich these members in the bordering frame 16. The frame 16 typically is made of relatively lightweight cardboard; and the structure, which has been described thus far, is in widespread use for disposable filters for forced g air handling heating and air conditioning systems.

The structure described above has been modified, in accordance with this invention, to place an elongated fibrous filler wick 26 in the space between the main or vertical portion 16 of at least part of the bordering frame on one or more sides and at least one of the inwardly-turned legs 16A or 16B, in the manner shown most clearly in FIG. 3. This elongated wick may be made with a triangular cross section, as illustrated in FIG. 3, or it may be an elongated or circular rectangular rod having dimensions which permit it to fit within the space shown and which typically exists in filters constructed as described above. While a fibrous, impregnated wick is preferred, semi-solid scented material also may be used.

The wick 26 imparts additional strength or rigidity to the frame 16; and the wick 26 is impregnated with a liquid or semisolid scented material of the type widely used for air fresheners in various forms. The material, with which the wick 26 impregnated, is selected to sublimate or volatilize when air passes through it. To facilitate such air passage, a series of spaced circular holes or apertures 20 are formed through the surface 16A of the border frame 16; and a corresponding set of spaced circular holes or apertures 22 are formed in the surface 16B throughout the full length or portions of one or more sides of the border frame 16 for the air filter unit.

As illustrated in FIGS. 2 and 3, the main air flow through the filter pad 14 takes place in a conventional manner. Nothing is placed in the normal filter area of the filter pad 14 and the grid 12 to impede this air flow in any way. The release of scented material, through the volatilization of the fragrance which is used to impregnate the filler wick 26, takes place through a secondary or supplemental air flow through the apertures 20 and 22, as illustrated in FIG. 3. This air flow is on the edges of the filter, as is readily apparent from an examination of FIGS. 1 and 2, and is considerably less than the main air flow passing through the primary body portion of the filter.

It is to be noted that the edges of the U-shaped border frame 16 rest on a supporting framework (not shown) within the duct work in which the filter is placed. Since the legs 16A and 16B, however, are inwardly-turned from the support plane of the border frame 16, air passes through the apertures 22 and 20 (as shown in FIG. 3) to effect the timed release of the scented material into the main airstream passing through the filter in its normal fashion.

The material for the filler wick 26, and the amount of scented formula, which is used to impregnate the wick 26, are selected so that the amount of scented material lasts for the average useful life of the filter material 14. The result is that a built-in signal is provided for changing the filter, when the scent no longer is present in the air passing through the forced air system into the various rooms serviced by that system. As a consequence, the person servicing the filter is less likely to forget to change the filter; and more efficient operation of the forced air system also will result, as a result of regular and frequent changing of the filter.

The material used to impregnate the filler wick 26 also may include an anti-bacterial and/or anti-fungal agent, which sublimates or volatilizes in a manner similar to the scented material used to impregnate the wick. In the alternative, for some applications, the scented material may be eliminated, and only bacterial or anti-fungal agents may be used to impregnate the wick 26 to provide control of bacteria, fungi and mold in the duct work of the air handling system, as well as in the rooms serviced by the system.

The foregoing description of the preferred embodiment of the invention should be considered as illustrative, and not as limiting. Various changes and modifications will occur to those skilled in the art, without departing from the true scope of the invention as defined in the appended claims.

I claim:

1. An air filter including in combination:
   a generally planar pad of air permeable filtering material having a predetermined thickness;
   a bordering frame for holding said pad of air permeable material, said frame having a generally U-shaped cross section comprised of a first portion perpendicular to the plane of said pad, with a width greater than said predetermined thickness, and having edges which terminate, respectively, in first and second inwardly turned legs extending a predetermined distance over and toward said pad of air permeable material to sandwich a part of said pad in said bordering frame, with the edges of said first portion lying in planes spaced from and parallel to the plane of said pad, said first and second legs of said frame having spaced apertures extending therethrough; and
   scented material placed within the region enclosed by said first and second inwardly-turned legs of said U-shaped cross section of said bordering frame, whereby air passes through the apertures in said first and second legs of said bordering frame through the part of said pad located within said region, and through said scented material.

2. The combination according to claim 1 wherein said bordering frame is made of cardboard.

3. The combination according to claim 2 wherein said scented material comprises a fibrous filler wick impregnated with scent.

4. The combination according to claim 3 wherein said fibrous filler wick provides reinforcing strength to said bordering frame.

5. The combination according to claim 4 wherein said fibrous filler wick is impregnated with a predetermined amount of scent for release at such a rate that after a predetermined time, no further scent is released by said fibrous filler wick, so that the absence of scent in the air filtered by said air filter is indicative of the need to replace said air filter.

6. The combination according to claim 5 wherein said scented material is placed within all parts of said bordering frame.

7. The combination according to claim 6 wherein said scent with which said fibrous filler wick is impregnated is a semi-solid, timed release scent formula.

8. The combination according to claim 7 further including volatile anti-bacterial/anti-fungal agents added to said scented material.

9. The combination according to claim 1 wherein said scented material comprises a filler wick impregnated with scent.

10. The combination according to claim 9 wherein said filler wick provides reinforcing strength to said bordering frame.

11. The combination according to claim 9 wherein said filler wick is impregnated with a predetermined amount of scent for release at such a rate that after a predetermined time, no further scent is released by said filler wick, so that the absence of scent in the air filtered by said air filter is indicative of the need to replace said air filter.

12. The combination according to claim 9 wherein said scent with which said filler wick is impregnated is a semi-solid timed release scent material.

13. The combination according to claim 1 wherein said scented material is placed within all parts of said bordering frame.

* * * * *